United States Patent [19]

Richter et al.

[11] 4,232,670
[45] Nov. 11, 1980

[54] TUBE TYPE SUPPLY CONTAINER FOR MEDICAL SYRINGE

[75] Inventors: Karl M. Richter, Wendtorf; Hans E. Harder, Probsteierhagen; Klaus Behrens, Rickling, all of Fed. Rep. of Germany

[73] Assignee: Howmedica International, Inc. Zweigniederlassung, Kiel, Fed. Rep. of Germany

[21] Appl. No.: 42,035

[22] Filed: May 24, 1979

[30] Foreign Application Priority Data

Jun. 30, 1978 [DE] Fed. Rep. of Germany ... 7819584[U]

[51] Int. Cl.³ .............................................. A61M 3/00
[52] U.S. Cl. ..................................... 128/224; 128/234
[58] Field of Search .................. 128/224, 234, 218 R, 128/218 P, 218 PA, 215, 216, 260, 261, 235

[56] References Cited

U.S. PATENT DOCUMENTS 742,434  10/1903  Hriss ..................................... 128/234

FOREIGN PATENT DOCUMENTS

| 71992 | 1/1951 | Denmark ............................... 128/218 P |
| 362556 | 3/1921 | Fed. Rep. of Germany ........... 128/234 |
| 365912 | 12/1922 | Fed. Rep. of Germany ....... 128/218 P |
| 887677 | 11/1943 | France .................................... 128/234 |
| 266921 | 8/1929 | Italy ......................................... 128/234 |
| 719752 | 9/1951 | United Kingdom ................. 128/218 P |

Primary Examiner—John D. Yasko
Attorney, Agent, or Firm—Andrus, Sceales, Starke & Sawall

[57] ABSTRACT

A tubular supply container for use in a medical syringe to dispense bone cement has a pipe formed tube with a slidable plunger. A smaller diameter injection pipe is removably secured to the forward end of the pipe formed tube. A funnel may also be applied to the forward end of the tube to assist in filling the container or may be placed on the rear end to serve as a stand.

6 Claims, 3 Drawing Figures

TUBE TYPE SUPPLY CONTAINER FOR MEDICAL SYRINGE

The invention relates to a tubular sypply container for use in a medical syringe for viscous media, in particular bone cement. The apparatus has a pipe-like tube, whose forward end is connected with a smaller diameter injection pipe, and a sealed and slidably movable plunger in the pipe-like tube.

A syringe is already known by which a pipe-like tube filled with a viscous medium is insertable in a channel formed support bar (DE-GM No. 7,607,385). In the manipulation of the syringe, a pusher rod is longitudinally displaceably supported in the thrust of a plunger in the tube. The known apparatus has the advantage of bringing measured quantities of sterilized materials in a simple manner within a short period of time to the desired location. Its use is of particularly great advantage in orthopedic surgery for the injection of bone cement in the treatment of bone fractures and/or the insertion of endoprotheses.

Bone cement is ordinarily manufactured from a pair of powder and liquid components. The pair of components are initially mixed in a separate container and subsequently loaded into the pipe-like tube. This procedure is however proportionately troublesome and time consuming.

The present invention has as its object to provide a tubular supply container for a medical syringe for viscous media, which results in a simple working of the viscous medium.

This object is achieved through the invention in that the forward end of the pipe-like tube is open and has securing means for the fastening of the injection pipe.

The invention proceeds from the recognition that the pipe-like tube open at both ends can be used at the same time as the mixing vessel. For this purpose the plunger is initially inserted in an assigned end of the tube and left in the initial position. Thereafter, the bone cement powder is introduced and the fluid component added. After the stirring of the mixture the injection pipe is then fastened on the tube and the assembled arrangement inserted in the syringe, as is known, for example from DE-GM No. 7,607,385. The mixing of the bone cement components in a separate vessel is avoided.

The supply container according to the invention is considered as a unitary article and is correspondingly formed of appropriate, but inexpensive plastic material.

With the invention, the injection pipe must be put on the tube after the production of the mixture, that is, be connected with the tube. Thus a preferred embodiment of the invention provides that the securing means comprises a thread, preferably a fast locking thread. It is of course possible, to provide the injection pipe with outer threads and the tube with inner threads in order to join the two parts to each other. It is preferably however, if, according to a further embodiment of the invention, the thread is formed on the outer side of the tube and on the inner side of the cylindrical section of the injection pipe. In order to assure the most advantageous transition possible between the tube and the injection pipe, another embodiment of the invention provides that the injection pipe has a conically flaring section on the rear end, the end of which is bringable into engagement with the securing means of the wall of the tube. Between the tube and the injection pipe a funnel shaped transition is thus produced.

The particular use of the supply container according to the invention is improved according to a further refinement of the invention in that a funnel is provided having a cylindrical part which can be pushed on the outer side of the tube and has a flaring conical part. On the inside of the cylindrical part a boss is provided which cooperates with the end surface of the tube. The funnel is set up with the cylindrical part on the open forward end surface of the tube and thus facilitates the filling with the components of the bone cement. After the filling the funnel is removed and pushed on the opposite end of the pipe formed tube, whereby the boss comes to lie against the rearward end surface of the tube. The funnel thus serves as a stand for the tube. The boss, which according to a further refinement of the invention, is formed from a ring-like band before the transition to the conical part also prevents falling out of the plunger formed stop.

After the mixing, the injection pipe is set up and the arrangement so formed, after removal of the funnel, inserted in the syringe.

The plunger usable for the invention can be formed in suitable manners and ways. A refinement of the invention thus provides that the plunger has a smooth forward cylindrical section and has a rear section formed with ring-like circular, flexible ribs, whereby the diameter of the cylindrical section corresponds to the inner diameter of the tube and the diameter of the ribs is somewhat greater than the inner diameter of the tube. With the insertion of the plunger in the inner cylinder of the tube, the flexible ribs are deformed somewhat rearward and inward, so that the plunger is held formlocked on the inner cylinder of the tube and is also self-holding therein.

An exemplary embodiment of the invention is more particularly explained with the aid of the following drawings.

Figure 1:
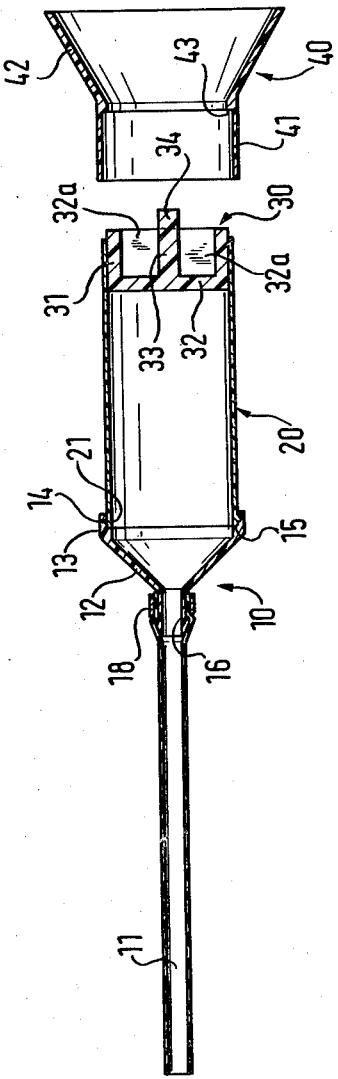
FIG. 1 shows a section through a supply container according to the invention.

The supply container shown in FIG. 1 is formed of four assembleable parts, namely a two-part injection pipe 10, a cylindrical tube 20, a plunger 30, and a funnel 40. The tube 20 is proportionately thin walled cylinder with a continuous inner bore, so that it is open at both ends. On the forward end a rapid locking thread 21 is formed on the outside.

Figure 3:
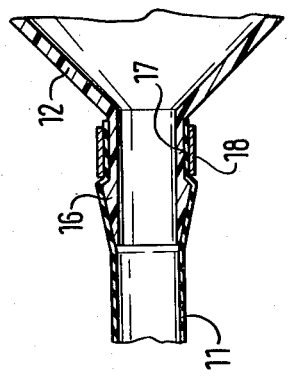
FIG. 3 shows a section through another portion of the supply container according to FIG. 1.

For functional efficiency, the injection pipe 10 is formed out of two parts, namely a proportionately long pipe section 11 with a proportionately small inner diameter, formed out of a quantity produced tubing which is cut to the desired length. Its fastening is shown in detail in FIG. 3. On the rear end the injection pipe 10 is connected with a conical section 12, which overlaps the outside of tube 20 with a cylindrical section 13 the outside of tube 20. An inner quick locking thread 14 of the conical section 12 coacts with thread 21 of the tube 20. On the inside of the cylindrical section 13 a shoulder 15 is formed against which the edge surface of tube 20 lies, whereby the inner diameter of the cylindrical section 13 is the same as that of tube 20, so that an even transition is established between the conical section 12 and tube 20. A boss 16 sits on the narrow portion of the conical section 12 over which the tubing 11 is drawn (FIG. 3).

The plunger 30 includes a cylindrical ring, which on the forward end is sealed through a massive disc 32. On the inside of the ring 31 are arranged perpendicularly crossing webs 32 and 33 connected with the disc formed part 32. From the crossing point of the webs 32, 33 extends rearwardly a peg 34 which coacts with a not shown pusher rod of the syringe.

Figure 2:
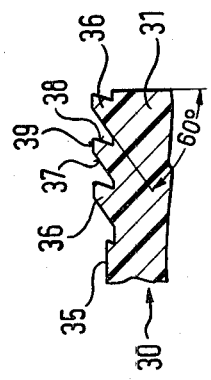
FIG. 2 shows a section through a portion of the plunger of the supply container according to FIG. 1.

The plunger ring 31 includes, as is apparent from FIG. 2, a section 35 the outer side of which is smoothly cylindrically formed. It extends approximately two-thirds of the length of the plunger. Thereafter are rearwardly attached three ring formed circular ribs 36, which are sawtoothed formed in cross-section such that the forward surfaces 37 join the longitudinal axis of plunger 30 at a smaller angle than the rear surfaces 38. The outside the ribs 36 form a smooth ring-formed section 39 which runs parallel and coaxial to the cylindrical section 35. The outer diameter of the cylindrical section 35 corresponds to the inner diameter of tube 20. The outer diameter of ribs 36 is somewhat greater than the inner diameter of the tube so that the ribs 36, with the insertion of the plunger 30, are elastically deformed rearwardly and radially inward.

The funnel 40 has a cylindrical part 41, the inner diameter of which corresponds approximately to the outer diamter of tube 20. A conical part 42 is joined to cylindrical part 42. In the transition between the cylindrical part 41 and the conical part 42 a ring-like band 43 formed, which functions as a boss when the funnel 40 is pushed over one of the two ends of tube 20. When the funnel is pushed over the forward end, it serves as a filling funnel. When it is pushed on the rear end, it serves as a stand and simultaneously prevents the pusher 30 from falling downwardly out of the tube.

The parts 10, 20, 30 and 40 can be manufactured out of a suitable plastic material. They are, before the use, preferably individually placed in a sterilized packing. The injection pipe 11 has a proportionately long length, for example up to 36 cm. Its material is so selected that a shortening with a scapel or sharp knife is possible for each desired length. In this way can also long shaft prostheses be provided.

The fastening of the tubing piece 11 on the boss 16 is apparent from FIG. 3. The shoulder 16 conically tapers to the forward end and has in the rear region an annulus (17) for the fastening of the tubing piece 11 by means of joinder ring 18 of stainless steel. The tubing piece 11 may also possibly rest sufficiently firmly on the shoulder 16 without a clamping collar (18) of this type. Customarily tubing piece 11 and section 12 are assembled at the time of manufacture.

We claim:

1. A tube-type supply container for viscous media, in particular bone cement, that is adapted to be inserted in an appliance provided with a manually actuable push rod, said supply container comprising:
    a cylindrical tube, both ends of said tube being open, one of said ends having first thread means adjacent thereto;
    injection pipe means including a relatively elongated pipe portion of relatively small diameter and a conically flared portion, said pipe portion being formed of a shearable, elastic material, said conically flared portion having second thread means by which the conically flared portion can be connected to one of the ends of said cylindrical tube by coaction with said first thread means;
    a plug-like piston that is sealingly displaceable within said cylindrical tube and adapted to be actuated by said push rod; and
    a funnel member having a cylindrical portion adapted to be slid on the outer side of either end of said cylindrical tube and having an abutment in its interior cooperating with either end face of said cylindrical tube.

2. A tube-type supply container set forth in claim 1, wherein said conically flared portion includes a tube-like extension adapted to be introduced into said elastic pipe portion and secured by a clamp.

3. The container according to claim 1 characterized in that a thread means (21) is formed on the outside of the tube (20) and on the inside of the cylindrical section (13) of the conically flared portion (12).

4. The container according to claim 1 characterized in that the abutment is formed of a ring-like band (43) in front of the transition to a conical part (42).

5. The container according to claim 1 characterized in that the plunger (30) has a forward cylindrical section (35) and a rearward formed section with ring-like circular flexible ribs (36), wherein the diameter of the cylindrical section (35) corresponds to the inner diameter of the tube (20) and the diameter of the ribs is somewhat greater than the diameter of the tube.

6. The container according to claim 5 characterized in that the ribs (36) have sawtoothed surfaces in cross-section, whereby when seen in the pushing direction, the forward surfaces (37) incorporate a smaller angle to the longitudinal axis than the rearward surfaces (38) and the apex of the ribs (36) is formed as a ring surface (39) parallel to the cylindrical section (35).

* * * * *